(12) United States Patent
Kohlstruk et al.

(10) Patent No.: US 7,420,080 B2
(45) Date of Patent: Sep. 2, 2008

(54) MULTISTAGE CONTINUOUS PREPARATION OF CYCLOALIPHATIC DIISOCYANATES

(75) Inventors: Stephan Kohlstruk, Duelmen (DE); Manfred Kreczinski, Herne (DE); Hans-Werner Michalczak, Herne (DE)

(73) Assignee: Degussa AG, Duesseldorf (DE)

( * ) Notice: Subject to any disclaimer, the term of this patent is extended or adjusted under 35 U.S.C. 154(b) by 490 days.

(21) Appl. No.: 11/101,428

(22) Filed: Apr. 8, 2005

(65) Prior Publication Data

US 2005/0267310 A1    Dec. 1, 2005

(30) Foreign Application Priority Data

May 29, 2004   (DE) ................. 10 2004 026 451

(51) Int. Cl.
*C07C 263/00*   (2006.01)
*C07C 249/00*   (2006.01)

(52) U.S. Cl. ........................................ 560/336

(58) Field of Classification Search ............. None
See application file for complete search history.

(56) References Cited

U.S. PATENT DOCUMENTS

| | | |
|---|---|---|
| 2,692,275 A | 10/1954 | Bortnick et al. |
| 3,919,279 A | 11/1975 | Rosenthal et al. |
| 4,081,472 A | 3/1978 | Tsumura et al. |
| 4,268,683 A | 5/1981 | Gurgiolo |
| 4,386,033 A | 5/1983 | Koenig et al. |
| 4,692,550 A | 5/1983 | Tyler |
| 4,530,796 A | 7/1985 | Mattner et al. |
| 4,596,678 A | 6/1986 | Merger et al. |
| 4,596,679 A | 6/1986 | Hellbach et al. |
| 4,713,476 A | 12/1987 | Merger et al. |
| 4,851,565 A | 7/1989 | Merger et al. |
| 5,087,739 A | 2/1992 | Bohmholdt et al. |
| 5,360,931 A * | 11/1994 | Bohmholdt et al. ......... 560/344 |
| 5,386,053 A | 1/1995 | Otterbach et al. |
| 5,418,260 A | 5/1995 | Smith |
| 5,453,536 A | 9/1995 | Dai et al. |
| 5,502,244 A | 3/1996 | Okawa et al. |
| 5,616,784 A | 4/1997 | Schwarz et al. |
| 5,646,328 A | 7/1997 | Deibele et al. |
| 5,744,633 A | 4/1998 | Wilmes et al. |
| 5,962,728 A | 10/1999 | Mason et al. |
| 6,204,409 B1 | 3/2001 | Aso et al. |
| 2005/0043561 A1 * | 2/2005 | Kohlstruk et al. ......... 560/345 |
| 2005/0043562 A1 | 2/2005 | Kohlstruck et al. |
| 2005/0043563 A1 * | 2/2005 | Kohlstruk et al. ......... 560/345 |

FOREIGN PATENT DOCUMENTS

| | | |
|---|---|---|
| DE | 1 022 222 | 1/1958 |
| DE | 196 27 552 A1 | 1/1998 |
| DE | 101 27 273 | 12/2002 |
| EP | 0 061 013 | 9/1982 |
| EP | 0 355 443 A2 | 2/1990 |
| EP | 0 355 443 A2 | 5/1990 |
| EP | 0 566 925 A2 | 10/1993 |
| EP | 0 568 782 A2 | 11/1993 |
| EP | 1 512 680 A1 | 3/2005 |

* cited by examiner

*Primary Examiner*—Karl J Puttlitz
(74) *Attorney, Agent, or Firm*—Oblon, Spivak, McClelland, Maier & Neustadt, P.C.

(57) ABSTRACT

The invention relates to a multistage process for continuous and phosgene-free preparation of cycloaliphatic diisocyanates.

53 Claims, No Drawings

MULTISTAGE CONTINUOUS PREPARATION OF CYCLOALIPHATIC DIISOCYANATES

BACKGROUND OF THE INVENTION

1. Field of the Invention

The invention relates to a multistage process for continuous and phosgene-free preparation of cycloaliphatic diisocyanates.

2. Discussion of the Background

The synthetic access route to isocyanates may be via a series of different routes. The variant for industrial scale preparation of isocyanates which is the oldest and still predominates today is what is known as the phosgene route. This process is based on the reaction of amines with phosgene. A disadvantage of the phosgene process is the use of phosgene which, as a consequence of its toxicity and corrosivity, places particularly high requirements on its handling on the industrial scale.

There are several processes which avoid the use of phosgene for preparing isocyanates on the industrial scale. The term phosgene-free process is frequently used in connection with the conversion of amines to isocyanates using alternative carbonylating agents, for example urea or dialkyl carbonate (U.S. Pat. Nos. 4,713,476; 5,087,739; 4,268,683; 6,204,409).

The urea route is based on the urea-mediated conversion of diamines to diisocyanates via a two-stage process. In the first step, a diamine is reacted with alcohol in the presence of urea or urea equivalents (for example alkyl carbonates, alkyl carbamates) to give a diurethane which typically passes through an intermediate purification stage and is then thermally cleaved in the second step to diisocyanate and alcohol (U.S. Pat. Nos. 5,087,739; 4,713,476; 5,386,053). Alternatively, the actual urethane formation may also be preceded by the separate preparation of a diurea by selectively reacting the diarnine with urea (U.S. Pat. No. 5,360,931). Also conceivable is a two-stage sequence consisting of partial reaction of urea with alcohol in the first and subsequent metering in and urethanization of the diamine in the second step (U.S. Pat. No. 5,744,633).

The thermal cleavage of urethanes to the corresponding isocyanates and alcohols has been known for some time and can be carried out either in the gas phase at high temperatures or at relatively low temperatures in the liquid phase. However, a problem in both procedures is that the thermal stress inevitably also causes undesired side reactions to take place which firstly reduce the yield and secondly lead to the formation of resinifying by-products which considerably disrupt the course of an industrial process as a result of deposits and blockages in reactors and workup apparatus.

There has therefore been no shortage of suggestions of chemical and process technology measures to achieve yield improvements and limit the undesired by-product formation. For instance, a series of documents describes the use of catalysts which accelerate the cleavage reaction of the urethanes (DE 10 22 222 and U.S. Pat. Nos. 3,919,279; 4,081,472). Indeed, it is entirely possible in the presence of suitable catalysts, which are a multitude of basic, acidic and also organometallic compounds, to increase the isocyanate yield in comparison to the uncatalyzed variant. However, the formation of undesired by-products can also not be prevented by the presence of a catalyst. The same applies to the additional use of inert solvents, as recommended in U.S. Pat. Nos. 3,919,279 and 4,081,472, in order to ensure uniform distribution of the heat supplied and of the catalyst in the reaction medium. However, the use of solvents boiling under reflux fundamentally has the consequence of a reduction in the space-time yield of isocyanates and is additionally hindered with the disadvantage of additional high energy demands.

Examples which are cited in U.S. Pat. No. 4,386,033 for thermal catalyzed cleavage of monourethanes describe the partial discharge of the reaction mixture to remove resinifying by-products formed in the course of the urethane cleavage. This procedure serves to prevent deposits and blockages in reactors and workup units. There are no indications which point to a yield-increasing utilization of the partial discharge. EP 061 013 describes a similar approach to a solution, in which the thermolysis is in this case carried out in the presence of solvents whose purpose is apparently to better absorb the involatile by-products. Here also, the partial discharge is not utilized for the purposes of yield optimization.

U.S. Pat. No. 5,087,739 discloses that a yield increase can be achieved when the higher molecular weight by-products which can and cannot be utilized and are formed in the cleavage reactor during the cleavage of diurethanes, to ensure a disruption-free and selective reaction, are discharged substantially continuously out of the reactor and subsequently converted for the most part in the presence of alcohol and then recycled into the diurethane preparation. The procedure described is associated with high energy demands, since nonutilizable by-products are removed from the effluent of the diurethane preparation by distillation, and all of the diurethane has to be evaporated. In contrast to U.S. Pat. No. 5,087,739, the urethanization effluent in the process of U.S. Pat. No. 5,386,053 is divided into two substreams of which only one is freed by distillation of its high-boiling, nonutilizable by-products, before the combined diurethane streams are fed to the deblocking reaction in the cleavage reactor. In addition, the continuous cleavage reactor discharge in U.S. Pat. No. 5,386,053 is recycled directly, i.e. without a reurethanization step, into the diurethane synthesis.

A consequence of the procedure described in U.S. Pat. No. 5,386,053 is that a portion of the high boiler components from the diurethane synthesis passes via the deblocking stage back into the diurethane preparation and further into the diurethane purification procedure.

OBJECT OF THE INVENTION

It is an object of the present invention to provide an improved process for preparing cycloaliphatic diisocyanates which avoids the above-mentioned disadvantages.

It has been found that, surprisingly, when cycloaliphatic diamines are used, it is advantageous to free the cycloaliphatic diurethanes of low and medium boilers after their synthesis by reaction of cycloaliphatic diamines with alcohol and urea and/or urea derivatives, to thermally cleave the cycloaliphatic diurethanes purified in this way to release the desired cycloaliphatic diisocyanate, to continuously discharge a portion of the cleavage residue from the cleavage apparatus and to reurethanize it with alcohol and thereafter to remove the high boiler components, and to recycle the stream purified in this way into the process. It has been found that this method firstly realizes a comparatively low steady-state concentration of high boiler components over the entire sequence of diurethane synthesis, diurethane purification and diurethane cleavage, so that deposits, which are promoted in particular by the high boiler components which are highly viscous by nature, can be substantially avoided, and also ensures good plant availability and good process yield even in the long term. Secondly, the sequence of reurethanization and high boiler removal downstream of the thermal cleavage reaction has the advantage that, in comparison to the customary procedure in which the high boilers are removed before the diurethane cleavage, the amount of diurethane to be converted to the vapor phase is significantly reduced, which allows capital and energy costs to be reduced.

DETAILED DISCUSSION OF THE INVENTION

The invention provides a multistage process for continuously preparing cycloaliphatic diisocyanates, by reacting cycloaliphatic diamines with carbonic acid derivatives and alcohols to give cycloaliphatic diurethanes and subsequently thermally cleaving the diurethanes to give cycloaliphatic diisocyanates, which comprises freeing the cycloaliphatic diurethanes of low and medium boilers after they have been synthetized by reacting cycloaliphatic diamines with alcohol and urea and/or urea derivatives, thermally cleaving the cycloaliphatic diurethanes purified in this way to release the desired diisocyanate, continuously discharging a portion of the cleavage residue from the cleavage apparatus and reurethanizing it with alcohol and thereafter removing the high boiler components, and recycling the stream purified in this way into the process.

The invention also provides a multistage process for continuously preparing cycloaliphatic diisocyanates of the formula (I)

OCN—R—NCO           (I)

where R is a bivalent cycloaliphatic hydrocarbon radical having from 4 to 18, preferably from 5 to 15, carbon atoms, with the proviso that the two nitrogen atoms are bonded directly to a hydrocarbon cycle and at least 3 carbon atoms are disposed between them, by reacting cycloaliphatic diamines with urea and/or urea derivatives and alcohols to give cycloaliphatic diurethanes and thermally cleaving them, wherein a) cycloaliphatic diamines of the formula (II)

H$_2$N—R—NH$_2$           (II)

where R is a bivalent cycloaliphatic hydrocarbon radical having from 4 to 18, preferably from 5 to 15, carbon atoms, with the proviso that the two nitrogen atoms are bonded directly to a hydrocarbon cycle and at least 3 carbon atoms are disposed between them, are reacted with urea and/or urea derivatives and alcohols of the formula (III)

R$^1$—OH           (III)

where R$^1$ is a radical as remains after removal of the hydroxyl group from a primary or secondary (cyclo)aliphatic alcohol having from 3 to 8 carbon atoms, in the absence or presence of dialkyl carbonates, alkyl carbamates or mixtures of dialkyl carbonates and carbamic esters, and in the absence or presence of catalysts, to give cycloaliphatic diurethanes, and the ammonia which is formed is removed simultaneously;

b) the alcohol, the dialkyl carbonates and/or alkyl carbamates are removed from the resulting reaction mixture and the alcohol and optionally also the dialkyl carbonates and/or alkyl carbamates are recycled in reaction stage a);

c) a removal of any high-boiling residues present in the resulting reaction mixture is fully or partially dispensed with;

d) the reaction mixture comprising the diurethanes purified by steps b) and c) is continuously and thermally cleaved in the presence of a catalyst continuously and without solvent, at temperatures of 180-280° C., preferably 200-260° C., and under a pressure of 0.1-200 mbar, preferably 0.2-100 mbar, in such a way that a portion of the reaction mixture of 10-60% by weight based on the feed, preferably 15-45% by weight based on the feed, is constantly discharged;

e) the cleavage products are separated by rectification into crude cycloaliphatic diisocyanate and alcohol;

f) the crude cycloaliphatic diisocyanate, purified by distillation, and the pure product fraction are isolated;

g) the bottoms discharge from d) is reacted partially or fully with the alcohol from e) in the presence or absence of catalysts within 1-150 min, preferably 3-60 min, at temperatures of 20-200° C., preferably 50-170° C., and at a pressure of 0.5-20 bar, preferably 1-15 bar, the molar ratio of NCO groups to OH groups being up to 1:100, preferably 1:20 and more preferably 1:10;

h) the reurethanized stream from g) is separated into a material-of-value stream and a waste stream, and the waste stream which is rich in high boiler components is discharged from the process and disposed of;

i) a portion of the bottoms fraction of the purification by distillation f) is continuously discharged and conducted into the cleavage reaction d) or into the urethanization stage g);

j) optionally, the top fraction obtained in the purification distillation f) of the crude cycloaliphatic diisocyanate is likewise recycled into the urethanization stage g);

k) the material-of-value stream from h) is recycled into stages a), b) or d).

In the process according to the invention, cycloaliphatic diisocyanates can be prepared continuously, without any problem and in very good yields. What is advantageous in the multistage process according to the invention is in particular the fact that even when cycloaliphatic diamines of the formula (II) are used as a starting material for the continuous diisocyanate synthesis, deposits, which are supported in particular by the high boiler components which are highly viscous by nature, can be substantially prevented and good plant availability and good process yield are ensured even in the long term. It is a further advantage of the multistage process according to the invention that it allows the amount of the diurethane to be converted to the vapor phase to be reduced to a minimum and in this way restricts the necessary energy demands.

a) To prepare the monomeric cycloaliphatic diurethanes in reaction stage a), the cycloaliphatic diamines of the formula (II) are reacted with urea and/or urea derivatives and an alcohol of the formula (III), optionally also mixtures of such alcohols, in a molar ratio of from 1:2.01:4.0 to 1:2.2:10, preferably from 1:2.02:6 to 1:2.12:9, optionally but not preferably in the presence of dialkyl carbonates, alkyl carbamates or mixtures of dialkyl carbonates and carbamic esters in an amount of in each case 1-10 mol % based on the diamine, in the absence or presence of catalysts, at reaction temperatures of 140-270° C., preferably 160-250° C., and under a pressure at which, depending on the alcohol used, is between 2-80 bar, preferably 7-15 bar, within from 2 to 20 hours, preferably 4-9 hours. The reaction may be effected in a continuous stirred tank battery, but preferably in a pressure distillation reactor.

To increase the reaction rate, the diurethanes may be prepared in the presence of catalysts. Suitable catalysts are inorganic or organic compounds which contain one or more, preferably a cation of, metals or Groups 1-15, in accordance with the IUPAC-recommended Periodic Table of the Elements; for example halides such as chlorides and bromides, sulfates, phosphates, nitrates, borates, alkoxides, phenoxides, sulfonates, oxides, oxide hydrates, hydroxides, carboxylates, chelates, carbonates and thio- or dithiocarbamates. Examples include the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Examples of typical catalysts include the following compounds: lithium ethoxide, lithium butoxide, sodium methoxide, potassium tert-butoxide, magnesium ethoxide, calcium methoxide, tin(II) chloride, tin(IV) chloride, lead acetate, aluminum trichloride, bismuth trichloride, copper(II) acetate, copper(II) chloride, zinc chloride, zinc octoate, titanium tetrabutoxide, vanadium trichloride, vanadium acetylacetonate, manganese(II) acetate, iron(II) acetate, iron(III) acetate, iron oxalate, cobalt chloride, cobalt naphthenate, nickel chloride, nickel naphthenate and mixtures thereof. The catalysts may optionally also be used in the form of their hydrates or ammoniates.

Starting compounds for the process according to the invention are cycloaliphatic diamines of the formula (II) which has already been mentioned above, alcohols of the formula (III) which has already been mentioned above, and also urea and/or urea derivatives (carbonic acid derivatives) suitable as a carboxylating agent, in the absence or presence of dialkyl carbonates, alkyl carbamates or mixtures of dialkyl carbonates and alkyl carbamates.

Suitable diamines of the formula (II) are, for example, 1,4-diaminocyclohexane, 4,4'-dicyclohexylmethanediamine, 2,4-dicyclohexylmethanediamine, 2,2'-dicyclohexylmethane-diamine and isomeric cycloaliphatic diamines, and also perhydrogenated diphenylmethanediamine. As a result of the preparation, diphenylmethanediamine (MDA) occurs as an isomer mixture of 4,4'-, 2,4- and 2,2'-MDA (see, for example, DE 101 27 273). Perhydrogenated diphenylmethanediamine is obtained by fully hydrogenating MDA and is accordingly a mixture of isomeric dicyclohexylmethanediamines ($H_{12}$NMA), i.e. 4,4'-, 2,4- and 2,2'-$H_{12}$MDA and possibly small amounts of (semi)aromatic MDA which has not been fully converted. The diamines of the formula (II) used are preferably 4,4'-dicyclohexylmethanediamine, 2,4-dicyclohexylmethanediamine and 2,2'-dicyclohexyl-methanediamine, and also any mixtures of at least two of these isomers. It will be appreciated that diamines may also be used which deviate from the formula (II). Examples include 1,3- and 1,4-diaminomethylcyclohexane, 1,6-hexanediamine, 2,2,4- or 2,4,4-trimethyl-1,6-hexan-amine and 3-aminomethyl-3,5,5-trimethylcyclohexylamine. However, preference is not given to using amines which deviate from the formula (II).

Suitable alcohols of the formula (III) are any aliphatic or cycloaliphatic alcohols which have a boiling point below 190° C. under atmospheric pressure. Examples include C1-C6-alkanols, for example methanol, ethanol, 1-propanol, i-propanol, 1-butanol, s-butanol, i-butanol, t-butanol, 1-pentanol, s-pentanol, i-pentanol, t-pentanol, 1-hexanol, s-hexanol, i-hexanol, t-hexanol, cyclohexanol, or mixtures thereof, preferably, methanol, ethanol, 1-propanol, 1-butanol, 2-butanol, 1-hexanol, cyclohexanol, or mixtures thereof; more preferably 1-butanol.

In the course of the conversion of the reaction mixture, ammonia is released, whose removal from the reaction equilibrium has been found to be advantageous. When ammonia is discharged from the reactor, care has to be taken that the wall temperatures of the reactor and of the discharge tube are above 60° C., so that deposition of ammonium carbamate, which is formed in minimal amounts from ammonia and carbon dioxide by decomposition of urea, can be prevented. It has been found to be useful, for example, to carry out the reaction in a pressure distillation reactor, in which case the reaction mixture is conducted in countercurrent to alcohol vapors introduced in the bottom and in this way such intensive mixing of the liquid proceeds on the trays that they each virtually correspond to a battery stage. The vaporous mixture of alcohol and ammonia which is withdrawn at the top may, preferably under the pressure of the pressure distillation reactor and without condensing it beforehand, be conducted into a distillation column, in order, from the ammonia, to obtain free alcohol which is recycled into the bottom of the pressure distillation reactor and of the column. In order to prevent fouling of the reflux condenser with ammonium carbamate, an appropriate proportion of alcohol is permitted therein to set the temperature at the top to at least 60° C.

b) The excess alcohol, the dialkyl carbonates, if they have been formed or are present in the reaction mixture, or alkyl carbamates or mixtures of at least two of these components are advantageously removed in two stages. At the first stage, the reaction mixture is decompressed from the pressure level of reaction stage a) to a pressure of 1-500 mbar, preferably 2-150 mbar, and in this way separated into gaseous vapors which contain the predominant amount of alcohol and also any dialkyl carbonates and/or alkyl carbamates, and into a liquid effluent. In the second stage, the liquid effluent is freed of any remaining residual alcohol and also medium boilers such as dialkyl carbonates and/or alkyl carbamates by thin-film evaporation at 180-250° C., preferably 200-230° C., and a pressure of 0.1-20 mbar, preferably 1-10 mbar, so that the residue consists substantially of the monomeric polyurethane, preferably diurethane, and in some cases high-boiling oligomers.

The vapors may, preferably after distillative purification, optionally be recycled into reaction stage a).

c) Preference is given to dispensing with any removal of any high boilers present in the reaction mixture from stage b). However, if the separation described under h) of the reurethanized stream from stage g) occurs only with one substream, i.e. partially, it may be advantageous to follow the routes for high boiler removal which are described below:

Optionally, the liquid stream from step b) which contains the monomeric diurethanes and any high-boiling oligomers and is obtained after the removal of low and medium boilers may be separated, preferably with the aid of a thin-film or short-path evaporator, at a temperature of 180-270° C., preferably 200-250° C., and under a pressure of 0.01-10 mbar, preferably 0.02-5 mbar, by distillation into a material-of-value stream which contains the monomeric diurethanes and the lower-boiling by-products and a nondistillable by-product stream. The nondistillable by-product stream which contains the high-boiling components is discharged from the preparative process and is typically discarded as a residue whose material cannot be utilized.

Optionally, the stream from stage b) which contains any high-boiling oligomers, before its above-described distillative purification, may also be divided into two substreams of which one is fed directly to the deblocking reaction (see d)) and the other initially passes through the high boiler removal described above.

d) The material-of-value stream from stage b) and optionally from stage c) which contains the monomeric diurethanes and the lower-boiling by-products is partly and continuously thermally cleaved in a suitable apparatus, without solvents in the liquid phase in the presence of catalysts at temperatures of 180-280° C., preferably 200-260° C., and under a pressure of 0.1-200 mbar, preferably 0.2-100 mbar. The conversion of diurethane to diisocyanate in the apparatus for thermal cleavage may, depending on the diurethane used, be selected substantially freely and is typically within the range of 10-95% by weight, preferably 35-85% by weight of the diurethane feed. The uncleaved proportion of the reaction mixture which contains unconverted diurethanes, high-boiling by-products and other reutilizable and nonutilizable by-products is continuously discharged. The amount of the discharge is governed, inter alia, by the desired conversion and the desired capacity of the cleavage reaction and can be easily determined experimentally. It is typically 10-60% by weight, preferably 15-45% by weight, based on the feed.

Useful catalysts for chemically cleaving the diurethanes are, for example, the aforementioned inorganic and organic compounds which catalyze urethane formation. Preference is given to using chlorides of zinc or tin, and also zinc oxides, manganese oxides, iron oxides or cobalt oxides, in which case the catalyst is metered into the stream comprising substantially diurethanes from the purification sequence b) and optionally c), before it is fed into the cleavage, as a 0.01-25% by weight, preferably 0.05-10% by weight, solution or suspension, preferably into the alcohol which is also used for urethane preparation, in an amount of 5-400 ppm, preferably 10-100 ppm.

Suitable cleavage apparatus is, for example, cylindrical cleavage reactors, for example tubular furnaces or preferably evaporators such as falling-film, thin-film or bulk evaporators, selected from Robert evaporators, Herbert evaporators, Caddle-type evaporators, Oskar evaporators and heating cartridge evaporators.

In principle, the main concern is to keep the average residence time of isocyanate groups, which are inevitably released when the alcohol is deblocked, in the cleavage zone very low and thus to limit undesired side reactions to a minimum.

Preference is given to carrying out the cleavage in a combined cleavage and rectification column, which is equipped for the energy supply in the bottom with a falling-film evaporator, in the lower third with a unit for additional energy input or for energy recovery, in the upper third with a unit to remove crude diisocyanate and at the top with a condenser for the reflux and the removal of pure alcohol.

e) The cleavage products which are formed in the thermal cleavage and are composed in particular of alcohol, diisocyanate and partially cleaved diurethanes are separated by rectification at 95-260° C., preferably 110-245° C., and a pressure of 0.5-250 mbar, preferably 1-100 mbar, into alcohol and into a crude diisocyanate mixture, preferably consisting of cycloaliphatic diisocyanate, partially cleaved cycloaliphatic diisocyanate and in some cases small amounts of cycloaliphatic diurethane. This separation may be carried out, for example, in the cleavage column of the abovementioned combined cleavage and rectification column.

f) The crude mixture which is preferably obtained by rectification, consisting of cycloaliphatic diisocyanate, partially cleaved cycloaliphatic diurethane and in some cases small fractions of cycloaliphatic diurethane, is purified by distillation at a temperature of 95-260° C., preferably 110-245° C., and under a pressure of 0.5-150 mbar, preferably 1-75 mbar, and the resulting fractions are recycled or isolated as a pure product.

g) The bottoms discharge from the cleavage stage d) is recycled partially or fully with the alcohol from the rectification stage e), the molar ratio of NCO groups to OH groups being up to 1:100, preferably 1:20 and more preferably 1:10, and the reaction mixture is reacted in the presence or absence of catalysts, within 1-150 min, preferably 3-60 min, at temperatures of 20-200° C., preferably 50-170° C. and a pressure of 0.5-20 bar, preferably 1-15 bar. The reaction may be carried out in a continuous tank battery or in a tubular reactor. Useful catalysts are in principle any catalysts which promote the NCO/OH reaction. Examples include tin octoate, dibutyl tin laurate, tin dichloride, zinc dichloride and triethylamine. The reurethanization may also be carried out in the presence of Fe(III) halides or Cu(I) halides or mixtures thereof. Examples include Fe(III) chloride, Fe(III) bromide, Cu(I) chloride and Cu(I) bromide. The use of these catalysts does not fundamentally rule out the simultaneous use of other catalysts which serve to accelerate the urethanization. Preference is given to using the halides of Fe(III) or Cu(I) or mixtures thereof without additionally using further catalysts.

h) The reurethanized stream from stage g) is separated into a material-of-value and a waste stream and the waste stream rich in high boiler components is discharged from the process and discarded. The two streams are separated preferably by distillation with the aid of a thin-film or short-path evaporator, at a temperature of 180-270° C., preferably 200-250° C., and under a pressure of 0.01-10 mbar, preferably 0.02-5 mbar. The material-of-value stream which comprises the monomeric diurethanes and the lower-boiling by-products is obtained as the distillate. The waste stream which is rich in high-boiling components is obtained as the residue and is discharged from the preparative process and typically discarded as a nonutilizable material. Alternatively, but not preferably, the separation into material-of-value and waste material may also be effected by extraction. An example of a suitable extractant is supercritical carbon dioxide.

Optionally, the reurethanized stream may also be divided into two substreams before the purification described above, from which one is fed directly to the purification stage b). The two substreams can be divided in a ratio of from 99:1 to 1:99, preferably from 95:5 to 5:95. Optionally, the reurethanized stream leading to the high boiler removal may initially be freed partly or fully of excess alcohol. This is preferably effected by distillation. The alcohol removed may be recycled as desired to stage a) or b).

i) A portion of the bottoms fraction of the purifying distillation f) is continuously discharged and optionally recycled into the cleavage stage d) or into the urethanization stage g). Preference is given to recycling into the urethanization stage. The amount of the discharge is 0.1-50% by weight, preferably 0.2-25% by weight, of the feed of crude polyisocyanate into the purifying distillation stage.

j) The top fraction of the purifying distillation stage f) may be discarded or preferably recycled into the urethanization stage g). The amount of top fraction removed per unit time is 0.1-3% by weight, preferably 0.3-1% by weight, of the feed of crude polyisocyanate into the purifying distillation.

k) The material-of-value stream from stage h) is recycled into the diurethane preparation a), the low and medium boiler removal b) or the diurethane cleavage d). Recycling into stage c) is also possible, but not preferred.

The multistage process according to the invention for continuously preparing cycloaliphatic diisocyanates with recycling and discharge of the by-products allows, for distillable cycloaliphatic diisocyanates, a reaction which proceeds without disruption and with high selectivity to be ensured over a prolonged period. The process according to the invention is suitable in particular for preparing cycloaliphatic diisocyanates having from 4 to 18, preferably from 5 to 15, carbon atoms, such as 1,4-diisocyanatocyclohexane, 4,4'-dicyclohexylmethane diisocyanate (4,4'-$H_{12}$MDI), 2,2'-dicyclohexylmethane diisocyanate (2,2'-$H_{12}$MDI), 2,4-dicyclohexylmethane diisocyanate (2,4-$H_{12}$MDI) or else mixtures of the aforementioned isomeric dicyclohexylmethane diisocyanates, as are obtained, for example, by the nature of the conversion of perhydrogenated MDA to $H_{12}$MDI.

The cycloaliphatic diisocyanates prepared are excellently suited to preparing polymers containing urethane, isocyanurate, amide and/or urea groups by the polyisocyanate polyaddition process. They additionally find use for preparing polyisocyanate mixtures modified with urethane, biuret and/or isocyanurate groups. Such polyisocyanate mixtures of cycloaliphatic diisocyanates are used in particular for preparing high-value, light-resistant polyurethane coatings.

The cycloaliphatic diisocyanates prepared are excellently suited to preparing polymers containing urethane, isocyanurate, amide and/or urea groups by the polyisocyanate polyaddition process. They additionally find use for preparing polyisocyanate mixtures modified with urethane, biuret and/or isocyanurate groups. Such polyisocyanate mixtures of cycloaliphatic diisocyanates are used in particular for preparing high-value, light-resistant polyurethane coatings.

For example, polymers containing urethane may be prepared by reacting the prepared cycloaliphatic diisocyanates with at least one polyol. At least one polyol may be selected from known polyols usually used in the production of polyurethanes.

Known polyols are those compounds that include dihydric alcohols having 2 to 20 carbon atoms (aliphatic diols, for instance, alkylene glycols such as ethylene glycol, diethylene glycol, propylene glycol, 1,3- or 1,4-butanediol, 1,6-hexanediol, and neopentylglycol; and alicyclic diols, for instance, cycloalkylene glycols such as cyclohexanediol and cyclohexanedimethanol); trihydric alcohols having 3 to 20 carbon atoms (aliphatic triols, for instance, alkane triols such as glycerol, trimethylolpropane, trimethylolethane, and hexanetriol, and triethanolamine); polyhydric alcohols having 4 to 8 hydroxyl groups and 5 to 20 carbon atoms (aliphatic polyols, for instance, alkane polyols and intramolecular or intermolecular dehydration products of the same such as pentaerythritol, sorbitol, mannitol, sorbitan, diglycerol, and dipentaerythritol; and saccharides and derivatives of the same such as sucrose, glucose, mannose, fructose, and methylglucoside).

Other mentionable polyols include monocyclic polyhydric phenols such as pyrogallol, hydroquinone and phloroglucinol; bisphenols such as bisphenol A, bisphenol F and bisphenol sulfone; and condensation products of phenols and formaldehyde (novolak).

Additionally, the above-mentioned polyols may include oligomers or polymers of alkylene oxides having 2 to 8 carbon atoms. The alkylene oxides include ethylene oxide, propylene oxide, 1,2-, 1,4-, 1-3, or 2,3-butylene oxide, styrene oxide, and the like.

Moreover, the above-mentioned polyols may include co-oligomers or co-polymers of alkylene oxides having 2 to 8 carbon atoms; wherein the alkylene oxides include combinations of two or more of ethylene oxide, propylene oxide, 1,2-, 1,4-, 1-3, or 2,3-butylene oxide, styrene oxide in block addition and/or random addition. Preferably, propylene oxide or a combination of propylene oxide and ethylene oxide (containing not more than 25 mass % of ethylene) is used.

Other examples of polyols include, but are not limited to, for example, aminic polyols such as JEFFAMINE™ as described in U.S. Pat. No. 5,418,260.

Having generally described this invention, a further understanding can be obtained by reference to certain specific examples which are provided herein for purposes of illustration only, and are not intended to be limiting unless otherwise specified.

EXAMPLES

Example: Preparation according to the invention of dicyclohexylmethane diisocyanate ($H_{12}$MDI) from perhydrogenated diphenylmethanediamine ($H_{12}$MDA) and urea in the presence of n-butanol.

Every hour, the uppermost tray of a pressure distillation reactor was charged with 281.5 g of $H_{12}$MDA, 164.1 g of urea and 599.7 g of n-butanol, and the reaction mixture was boiled at 220° C. and an average residence time of 8.5 hours while continuously removing the ammonia released at 11-14 bar. The reactor effluent, together with the stream from the high boiler removal, was subsequently freed of excess alcohol, low boilers and medium boilers in the flash vessel at 55 mbar with subsequent thin-film evaporation at 220° C. and 2 mbar, and the remaining 780.5 g/h of bis(4-butoxycarbonylaminocyclohexyl)methane ($H_{12}$MDU) were conducted as a melt (140° C.) into the circulation of the falling-film evaporator of the cleavage and rectification column, and the deblocking reaction was carried out at a temperature of 232° C. and a bottom pressure of 9 mbar in the presence of a steady-state concentration of tin dichloride of 20 ppm. The cleavage gases, $H_{12}$MDI and butanol, were condensed out in two condensers connected in series at 85° C. and −25° C. The resulting about 97% crude $H_{12}$MDI was fed to a purifying distillation where 321.3 g/h of $H_{12}$MDI having a purity of >99.5% were obtained, which corresponds to a yield of 92%. 228.1 g/h of butanol were obtained as the top product of the cleavage and rectification column. To maintain constant mass within the cleavage and rectification column and avoid fouling and blockages of the cleavage apparatus, a substream was continuously discharged from the circuit and, together with 23.9 g/h of bottoms discharge from the $H_{12}$MDI purifying distillation and the top product from the cleavage and rectification column, purified and reurethanized. The reurethanized stream was freed of excess butanol by flash evaporation at 40 mbar and separated by means of a short-path evaporator at 235° C. and a pressure of 0.04 mbar into a waste stream rich in high boilers and a material-of-value stream. The 231.1 g/h of material-of-value stream were fed to the flash vessel together with the reactor effluent of the diurethane preparation.

This application is based on DE Application No. 10 2004 026 451.1, filed with the German patent office on May 29, 2004, the entire contents of which is hereby incorporated herein by reference.

Obviously, numerous modifications and variations on the present invention are possible in light of the above teachings. It is therefore to be understood that within the scope of the appended claims, the invention may be practiced otherwise than as specifically.

What is claimed as new and is intended to be secured by Letters Patent is:

1. A multistage process for continuously preparing a cycloaliphatic diisocyanate, comprising:
   reacting a cycloaliphatic diamine with urea and/or an urea derivative and an alcohol to give a cycloaliphatic diurethane;
   freeing the cycloaliphatic diurethane of low and medium boilers, to obtain a purified cycloaliphatic diurethane;
   subsequently thermally cleaving the purified cycloaliphatic diurethane in a cleavage apparatus to give a cycloaliphatic diisocyanate and a cleavage residue,
   continuously discharging a portion of the cleavage residue from the cleavage apparatus and reurethanizing said portion of the cleavage residue with alcohol, to obtain a reurethanized stream; and thereafter removing high boiler components from said reurethanized stream, and recycling the reurethanized stream into the process into at least one step selected form the group consisting of the diurethane preparation, the low and medium boiler removal, and the diurethane cleavage.

2. A multistage process for continuously preparing a cycloaliphatic diisocyanate of the formula (I)

$$OCN-R-NCO \quad (I)$$

wherein R is a bivalent cycloaliphatic hydrocarbon radical having from 4 to 18, carbon atoms, with the proviso that the two nitrogen atoms are bonded directly to a hydrocarbon cycle and at least 3 carbon atoms are disposed between said two nitrogen atoms, by reacting a cycloaliphatic diamine with urea and/or an urea derivative and an alcohol to give a cycloaliphatic diurethane and thermally cleaving said cycloaliphatic diurethane, said process comprising:

a) reacting a cycloaliphatic diamine of the formula (II)

$$H_2N-R-NH_2 \quad (II)$$

wherein R is a bivalent cycloaliphatic hydrocarbon radical having from 4 to 18, carbon atoms, with the proviso that the two nitrogen atoms are bonded directly to a hydrocarbon cycle and at least 3 carbon atoms being disposed between said two nitrogen atoms, with urea and/or an urea derivative and an alcohol of the formula (III)

$$R^1-OH \quad (III)$$

wherein $R^1$ is a radical as remains after removal of the hydroxyl group from a primary or secondary (cyclo) aliphatic alcohol having from 3 to 8 carbon atoms, in the absence or presence of a dialkyl carbonate, an alkyl carbamate or mixtures of a dialkyl carbonate and a carbamic ester and in the absence or presence of a catalyst, to give a cycloaliphatic diurethane, and ammonia formed is simultaneously removed;

b) removing the alcohol, the dialkyl carbonate and/or alkyl carbamate from the resulting reaction mixture, and recycling into the reaction stage a) the alcohol and optionally also the dialkyl carbonate and/or alkyl carbamate;

c) optionally, removing any high-boiling residues present in the resulting reaction mixture and fully or partially dispensing with the high-boiling residue;

d) continuously and thermally cleaving without solvent in the presence of a catalyst the reaction mixture comprising the diurethanes purified by steps b) and optionally c) at temperatures of from 180° C. to 280° C., and under a pressure of from 0.1 mbar to 200 mbar, thereby obtaining a cleavage product; said cleaving proceeding in such a way that a portion of the reaction mixture of from 10 to 60% by weight based on the feed, is constantly discharged as a bottoms discharge, e) separating by rectification the cleavage product into crude cycloaliphatic diisocyanate and alcohol;

f) purifying by distillation the crude cycloaliphatic diisocyanate, and isolating a pure cycloaliphatic diisocyanate product fraction;

g) reacting the bottoms discharge from d) partially or fully with the alcohol from e), in the presence or absence of a catalyst, within from 1 min to 150 min, at temperatures of from 20° C. to 200° C., and at a pressure of from 0.5 bar to 20 bar, a molar ratio of NCO groups to OH groups being up to 1:100, thereby obtaining a reurethanized stream;

h) separating the reurethanized stream from g) into a material-of-value stream and a waste stream, and discharging and discarding the waste stream rich in high boiler components from the process;

i) continuously discharging and conducting a portion of the bottoms fraction of the purification by distillation f) into the cleavage reaction d) or into the urethanization stage g);

j) optionally recycling the top fraction obtained in the purification by distillation f) of the crude cycloaliphatic diisocyanate into the urethanization stage g);

k) recycling the material-of-value stream from h) into stage a), b) or d).

3. The multistage process of claim 1 or claim 2, wherein the cycloaliphatic diamine is selected from the group consisting of 4,4'-dicyclohexylmethanediamine, 2,4-dicyclohexylmethanediamine, 2,2'-dicyclohexylmethanediamine, and mixtures thereof.

4. The multistage process of claim 1 or claim 2, wherein the cycloaliphatic diamine is selected from the group consisting of 4,4'-dicyclohexylmethanediamine, a isomeric cycloaliphatic diamine, and mixtures thereof.

5. The multistage process of claim 1 or claim 2, wherein the cycloaliphatic diamine is 1,4-diaminocyclohexane.

6. The multistage process of claim 2, wherein stage a) occurs continuously in a distillation reactor or in a stirred tank battery.

7. The multistage process of claim 2, wherein the reaction in stage a) is effected in a molar ratio of diamine:urea:alcohol of from 1:2.01:4.0 to 1:2.2:10.

8. The multistage process of claim 2, wherein the residence time of the reactants in stage a) is from 2 hours to 10 hours.

9. The multistage process of claim 2, wherein stage a) occurs in a reactor at from 140° C. to 270° C. and a pressure of from 2 bar to 80 bar.

10. The multistage process of claim 2, wherein the reaction in stage a) occurs at reaction temperatures of from 160° C. to 250° C. and a pressure of from 7 bar to 15 bar.

11. The multistage process of claim 2, wherein stage a) occurs in the pressure distillation reactor.

12. The multistage process of claim 2, wherein, in stage a), the reactants are supplied continuously to the uppermost tray and the ammonia released is driven out supported by alcohol vapors which are introduced into the bottom of the distillation reactor.

13. The multistage process of claim 2, wherein, in stage a), alcohols having 1-6 carbon atoms are used.

14. The multistage process of claim 2, wherein, in stage a), butanol is used.

15. The multistage process of claim 2, wherein the reaction in stage a) occurs in the presence of catalysts.

16. The multistage process of claim 2, wherein stage b) occurs in two stages.

17. The multistage process of claim 16, wherein, at the first stage, the reaction mixture is decompressed from the pressure level of reaction stage a) to a pressure of from 1 mbar to 500 mbar.

18. The multistage process of claims 16 or 17, wherein, in the second step, the liquid effluent is freed of any residual alcohol present and also of medium boilers such as dialkyl carbonates and/or alkyl carbamates by thin-film evaporation at from 180° C. to 250° C., and a pressure of from 0.1 mbar to 20 mbar.

19. The multistage process of claims 16 or 17, wherein the vapors of stage b) are fed, after further distillative purification, into reaction stage a).

20. The process of claim 2, wherein the separation in stage c), if employed, occurs at a temperature of from 180° C. to 270° C., and under a pressure of from 0.01 mbar to 10 mbar.

21. The multistage process of claim 2, wherein stage c), if employed, occurs with the aid of a thin-film or short-path evaporator.

22. The multistage process of claim 2, wherein the by-products from stage c), if employed, are discharged and discarded.

23. The multistage process of claim 2, wherein the stream in stage c), if this is employed, is processed in such a way that it is divided before its distillative purification into two substreams of which one substream is fed directly to the cleavage reaction (step d).

24. The multistage process of claim 2, wherein the thermally induced diurethane cleavage of stage d) occurs in at least one tubular furnace or in at least one evaporator.

25. The multistage process of claim 2, wherein the stage d) occurs in a combined cleavage and rectification column.

26. The multistage process of claim 2, wherein, in stage d), thermal cleavage is effected continuously at temperatures of from 180° C. to 280° C., and under a pressure of from 0.1 mbar to 200 mbar.

27. The multistage process of claim 2, wherein, in stage d), cleavage is effected without solvent in the liquid phase.

28. The multistage process of claim 2, wherein stage d) occurs in the presence of catalysts.

29. The multistage process of claim 2, wherein, in stage d), the conversion of diurethane to diisocyanate is selected within the range of from 10% by weight to 95% by weight of the diurethane feed.

30. The multistage process of claim 2, wherein, in stage d), a portion of the reaction mixture which comprises unconverted diurethanes, high-boiling by-products and other reutilizable and nonutilizable by-products is continuously discharged.

31. The multistage process of claim 30, wherein the amount of the discharge is from 10% by weight to 60% by weight based on the feed.

32. The multistage process of claim 2, wherein stage e) occurs in a combined cleavage and rectification column.

33. The multistage process of claim 2, wherein operation is effected at temperatures of from 95° C. to 260° C. and a pressure of from 0.5 mbar to 250 mbar.

34. The multistage process of claim 2, wherein, in stage f), the crude fraction obtained from stage e), consisting of cycloaliphatic diisocyanate, partially cleaved cycloaliphatic diurethane and in some cases small fractions of cycloaliphatic diurethane, is purified by distillation at a temperature of from 95° C. to 260° C. and under a pressure of from 0.5 mbar to 150 mbar.

35. The multistage process of claim 34, wherein the fraction obtained in stage f) is isolated as a pure product or recycled into stage g).

36. The multistage process of claim 2, wherein, in stage h), operation is effected at a temperature of from 180° C. to 270° C., and under a pressure of from 0.01 mbar to 10 mbar.

37. The multistage process of claim 2, wherein in stage h), operation is effected distillatively with the aid of a thin-film or short-path evaporator.

38. The multistage process of claim 2, wherein stage h) is effected by extraction.

39. The multistage process of claim 2, wherein the reurethanized stream from g), before the distillative purification, is optionally divided into two substreams, of which one is fed directly to the purificaction stage b).

40. The multistage process of claim 39, wherein the two substreams are divided in a ratio of from 99:1 to 1:99.

41. The multistage process of claim 2, wherein stage i) occurs in a continuous tank battery or in a tubular reactor.

42. The multistage process of claim 2, wherein the reaction in stage g) occurs in the presence of a catalyst selected from the group consisting of a tin carboxylate, a tin halide, a zinc carboxylate, a zinc halide, a tertiary amine, a Cu(I) halide, an Fe(III) halide, and combinations thereof.

43. The multistage process of claim 2, wherein, in stage i), the recycling is effected into the urethanization stage g).

44. The multistage process of claim 2, wherein, in stage j), the amount of the discharge is from 0.1% by weight to 50% by weight of the feed of crude polyisocyanate into the purifying distillation stage.

45. The multistage process of claim 2, wherein the amount of top fraction removed per unit time in step j) is from 0.1% by weight to 3% by weight of the feed of crude diisocyanate into the purifying distillation.

46. The multistage process of claim 2, wherein the reurethanized stream from g) leading to the high boiler removal h) is initially freed partially or fully of excess alcohol and the alcohol removed is recycled as desired into stage a) or b).

47. A multistage process of claim 2, wherein the material-of-value stream from the high boiler removal h) is recycled into stage a), b) or d).

48. The multistage process of claim 2, wherein 1,4-diisocyanatocyclohexane, 4,4'-dicyclohexylmethane diisocyanate, 2,2' dicyclohexylmethane diisocyanate, 2,4-dicyclohexylmethane diisocyanate or else any mixtures of at least two isomeric dicyclohexylmethane diisocyanates are prepared.

49. The multistage process of claim 2, wherein diamines selected from 1,3 and 1,4-diaminomethylcyclohexane, hexane-1,6-diamine, 2,2,4 and 2,4,4-trimethylhexan-1,6-amine and 3 aminomethyl-3,5,5-trimethylcyclohexylamine are used.

50. The multistage process of claim 1, which further comprises reacting the cycloaliphatic diisocyanate with a polyol.

51. The multistage process of claim 1, which further comprises reacting the cycloaliphatic diisocyanate with a diol.

52. The multistage process of claim 2, which further comprises reacting the cycloaliphatic diisocyanate with a polyol.

53. The multistage process of claim 2, which further comprises reacting the cycloaliphatic diisocyanate with a diol.

* * * * *

UNITED STATES PATENT AND TRADEMARK OFFICE
CERTIFICATE OF CORRECTION

PATENT NO. : 7,420,080 B2
APPLICATION NO. : 11/101428
DATED : September 2, 2008
INVENTOR(S) : Stephan Kohlstruk et al.

Page 1 of 1

It is certified that error appears in the above-identified patent and that said Letters Patent is hereby corrected as shown below:

On the title page, the Terminal Disclaimer information has been omitted. Item (45) and the Notice should read as follows:

On the Title Page, Item
-- (45) Date of Patent: *Sep. 2, 2008

(*) Notice: Subject to any disclaimer, the term of this patent is extended or adjusted under 35 U.S.C. 154(b) by 490 days.

This patent is subject to a terminal disclaimer. --

Signed and Sealed this

Fourth Day of November, 2008

JON W. DUDAS
*Director of the United States Patent and Trademark Office*